United States Patent [19]

Florance et al.

[11] Patent Number: 4,489,071

[45] Date of Patent: Dec. 18, 1984

[54] BETAMETHASONE DIPROPIONATE CREAM

[75] Inventors: Richard K. Florance, Boonton, N.J.; Joel A. Sequeira, New York, N.Y.

[73] Assignee: Schering Corporation, Madison, N.J.

[21] Appl. No.: 559,671

[22] Filed: Dec. 9, 1983

[51] Int. Cl.³ .............................................. A61K 31/56
[52] U.S. Cl. .................................................... 424/243
[58] Field of Search ......................................... 424/243

[56] References Cited

U.S. PATENT DOCUMENTS 4,070,462  1/1978  Ecker ................................... 424/243

Primary Examiner—Elbert L. Roberts
Attorney, Agent, or Firm—Warrick E. Lee, Jr.; Stephen I. Miller; Bruce M. Eisen

[57] ABSTRACT

An elegant topical cream composition, containing betamethasone dipropionate, for the treatment of inflammation.

8 Claims, No Drawings

BETAMETHASONE DIPROPIONATE CREAM

This invention relates to a cream formulation of betamethasone dipropionate having improved properties.

U.S. Pat. No. 4,070,462 discloses a steroid ointment having very good efficacy. The effectiveness of this composition is believed to be due to the steroid's being completely dissolved in the ointment. However, this ointment, like others, feels somewhat greasy when applied to the skin. Another product currently on the market (Diprosone Cream) is an oil-in-water emulsion containing, in addition to the betamethasone dipropionate, water, mineral oil, white petrolatum, ceteth 20, cetostearyl alcohol, monobasic sodium phosphate, and phosphoric acid, preserved with 4-chloro-m-cresol and propylene glycol. While this formula is more cosmetically elegant than the previously discussed ointment, it is not as effective.

U.S. patent application Ser. No. 494,214, filed May 13, 1983, (having assignee in common with the present patent application) discloses a cream-like composition having better efficacy than Diprosone Cream.

The present invention provides a betamethasone dipropionate cream formulation having cosmetic elegance and, very surprisingly, efficacy similar to the ointment of U.S. Pat. No. 4,070,462. This is particularly unexpected in view of the fact that the present invention is in the form of a water-in-oil emulsion, throughout which the steroid is dispersed, i.e., the steroid is not completely dissolved. Furthermore, the compositions are surprisingly stable for water-in-oil emulsions.

Some steroidal ointments have a tendency to suppress the hypopituitary adrenal (HPA) axis, causing a potentially dangerous decrease in the level of cortisol in the blood. The present compositions show little, if any, tendency to cause HPA-axis suppression.

SUMMARY OF THE INVENTION

The present invention comprises an esthetically elegant topical composition for the treatment of inflammation in the form of a water-in-oil emulsion comprising by weight based on the total weight of the composition:

(a) 0.02 to 0.1 percent betamethasone dipropionate, (b) 15 to 40 percent white petrolatum (preferably 20 to 30 percent), (c) 3 to 15 percent white wax (preferably 7 to 12 percent), (d) 5 to 25 percent solution of 70% sorbitol in water (preferably 10 to 20 percent), (e) 2.5 to 15 percent propylene glycol (preferably 3 to 8 percent), (f) buffer to maintain the pH of the composition within the range of 3 to 6, (g) sufficient amounts of at least one hydrophilic emulsifier and at least one lipophilic emulsifier to stabilize the emulsion and disperse the betamethasone dipropionate, wherein the HLB of the emulsifiers is within the range of 2 to 8 (preferably 4 to 6), (h) sufficient dermatologically acceptable preservative to prevent degradation of the composition by microorganisms, and (i) water.

Preferably the formulations contain from 3 to 15 percent cyclomethicone (more preferably 5 to 10 percent). The preferred buffer system comprises 0.3 percent monobasic sodium phosphate monohydrate and 0.001 percent phosphoric acid. Other buffer systems, for example a combination of citric acid monohydrate and trisodium citrate dihydrate or succinic acid and sodium hydroxide may be used.

The preferred hydrophilic emulsifier is ceteth 20, in the amount of 0.01 to 2 percent, preferably 0.3 to 0.7 percent. Other hydrophilic emulsifers for use in the compositions include polyoxyethylene sorbitan monooleate, polyoxyethylene monostearate, polyoxyethylene lauryl ether, and polysorbate 60 and combinations thereof.

The preferred lipophilic emulsifier is glyceryl oleate in the amount of 1 to 5 percent, preferably 2 to 4 percent. Other acceptable lipophilic emulsifiers include sorbitan tristearate, glyceryl stearate, propylene glycol stearate sorbitan sesquioleate and combinations thereof The HLB is defined by Griffin, W. C., J. Soc. Cosmetic Chemist, 1, 311 [1949]and 5, 249 [1954]. The HLB reflects the balance between hydrophilic and lipophilic strength of the emulsifiers. The higher HLB, indicates a stronger hydrophilic tendency of the emulsification system.

The preferred preservative is 0.03 to 0.2 percent 4-chloro-m-cresol (preferably 0.07 to 0.12 percent). Other acceptable preservatives include benzyl alcohol, sorbic acid, methyl paraben, propyl paraben, and combinations thereof.

All percentages are by weight. The definitions of components whose chemical composition is not immediately clear from the name used, such as "ceteth 20", may be found in the CTFA Cosmetic Ingredients Dictionary, 3rd Edition, published by the Cosmetic, Toiletry, and Fragrance Association, Inc., Washington, D.C.

EXAMPLE 1

| Ingredient | Quantity, mg/g of Emulsion |
| --- | --- |
| betamethasone dipropionate | 0.64 |
| white petrolatum, USP | 250 |
| white wax flakes, NF | 100 |
| cyclomethicone | 70 |
| glyceryl oleate | 30 |
| ceteth 20 | 0.5 |
| solution of 70% sorbitol in water | 150 |
| 4-chloro-m-cresol | 1 |
| propylene glycol | 50 |
| monobasic sodium phosphate monohydrate | 2.65 |
| phosphoric acid, NF | 0.01 |
| purified water, USP | q.s. ad 1 g. |

PROCEDURE

1. Heat about 80 percent of the water to 70° C. Dissolve the monobasic sodium phosphate monohydrate, 4-chloro-m-cresol, and propylene glycol in the heated water. Adjust the pH to 4.5 with a 1 percent solution of phosphoric acid in water.

2. To a separate vessel charge the white petrolatum, white wax flakes, and glycerol oleate, propylene glycol mixture. Melt and heat to 75° C. with agitation. Charge the sorbitol solution and cyclomethicone while maintaining 70° C.

3. Combine the mixtures resulting from steps 1 and 2 with rapid agitation and cool the combination to 35° C. with medium agitation.

4. Heat the remaining portion of the water to 65° C. in a separate vessel and dissolve the ceteth-20 therein. Cool to 35° C.

5. To about 90 percent of the solution of step 4, charge the betamethasone dipropionate and mill until a uniform dispersion is obtained.

6. Add the milled dispersion from step 5 and the remainder of the ceteth-water mixture from step 4 to the combination of step 3. Mix at 35° C. until uniform. Cool the batch to room temperature with slow agitation.

EXAMPLE 2

| Ingredient | Quantity mg/g of Emulsion |
|---|---|
| betamethasone dipropionate | 0.64 |
| white petrolatum USP | 300. |
| white wax flakes NF | 70. |
| cyclomethicone | 50. |
| glyceryl oleate | 30. |
| ceteth 20 | 0.5 |
| solution of 70% sorbitol in water | 150. |
| 4-chloro-m-cresol | 1. |
| propylene glycol | 50. |
| citric acid monohydrate | 0.7 |
| trisodium citrate dihydrate | 1.9 |
| purified water USP | q.s. ad 1 g. |

The ingredients are combined in a manner similar to example 1.

EXAMPLE 3

| Ingredient | Quantity mg/g of Emulsion |
|---|---|
| betamethasone dipropionate | 0.64 |
| white petrolatum USP | 200 |
| white wax flakes NF | 100 |
| cyclomethicone | 100 |
| glyceryl oleate | 30 |
| ceteth 20 | 0.5 |
| solution of 70% sorbitol in water | 150 |
| benzyl alcohol | 10 |
| propylene glycol | 50 |
| monobasic sodium phosphate monohydrate | 2.65 |
| phosphoric acid NF | 0.01 |
| purified water USP | q.s. ad 1 g. |

The ingredients are combined in a manner similar to example 1.

EXAMPLE 4

| Ingredient | Quantity mg/of Emulsion |
|---|---|
| betamethasone dipropionate | 0.64 |
| white petrolatum USP | 300 |
| white wax flakes NF | 50 |
| cyclomethicone | 50 |
| sorbitan sesquioleate | 40 |
| polysorbate 60 | 10 |
| solution of 70% sorbitol in water | 100 |
| 4-chloro-m-cresol | 1 |
| propylene glycol | 50 |
| monobasic sodium phosphate monohydrate | 2.65 |
| phosphoric acid NF | 0.01 |
| purified water USP | q.s. ad 1 g. |

The ingredients are combined in a manner similar to example 1.

When applied to the skin, the formulations of the examples are found to be equivalent to the ointment of U.S. Pat. No. 4,070,462, in vasoconstrictor and anti-inflammatory activity, despite its being in the form of an elegant cream. Furthermore, formulas of the present invention have little or no tendency to suppress the HPA axis.

What is claimed is:

1. An elegant topical composition for the treatment of inflammation comprising by weight based on the total weight of the composition:
   (a) 0.02 to 0.1 percent betamethasone dipropionate,
   (b) 15 to 40 percent white petrolatum,
   (c) 3 to 15 percent white wax,
   (d) 5 to 25 percent solution of 70% sorbitol in water,
   (e) 2.5 to 15 percent propylene glycol,
   (f) buffer to maintain the pH of the composition within the range of 3 to 6,
   (g) sufficient amounts at least one hydrophilic emulsifier and at least one lipophilic emulsifier to stabilize the emulsion and disperse the betamethasone dipropionate, wherein the HLB of the emulsifier is within the range of 2 to 8,
   (h) sufficient dermatologically acceptable preservative to prevent degradation of the composition by microorganisms, and
   (i) water.

2. The composition of claim 1 wherein:
the amount of white petrolatum is 20 to 30 percent,
the amount of white wax is 7 to 12 percent,
the amount of sorbitol solution is 10 to 20 percent,
the amount of propylene glycol is 3 to 8 percent, and
the HLB of the emulsifiers is within the range of 4 to 6.

3. The composition of claim 2 further comprising:
(j) 3 to 15 percent cyclomethicone.

4. The composition of claim 1 further comprising:
(j) 3 to 15 percent cyclomethicone.

5. The composition of claim 4 comprising:
(a) 0.06 percent betamethasone dipropionate,
(b) 25 percent white petrolatum,
(c) 10 percent white wax,
(d) 15 percent solution of 70% sorbitol in water,
(e) 5 percent propylene glycol,
(f) 0.3 percent monobasic sodium phosphate monohydrate and 0.001 percent phosphoric acid,
(g) 0.05 percent ceteth 20 and 3 percent glycerol oleate,
(h) 0.1 percent 4-chloro-m-cresol,
(i) water, and
(j) 7 percent cyclomethicone.

6. The composition of claim 4 comprising:
(a) 0.06 percent betamethasone dipropionate,
(b) 30 percent white petrolatum,
(c) 7 percent white wax,
(d) 15 percent solution of 70% sorbitol in water,
(e) 5 percent propylene glycol
(f) 0.07 percent citric acid monohydrate and 0.2 percent trisodium citrate dihydrate,
(g) 0.05 percent ceteth 20 and 3 percent glyceryl oleate,
(h) 0.1 percent 4-chloro-m-cresol,
(i) water, and
(j) 5 percent cyclomethicone 7. The composition of claim 4 comprising:
(a) 0.06 percent betamethasone dipropionate, (b) 20 percent white petrolatum,
(c) 10 percent white wax,
(d) 15 percent solution of 70% sorbitol in water,
(e) 5 percent propylene glycol,
(f) 0.001 phosphoric acid and 0.3 percent monobasic sodium phosphate monohydrate,
(g) 0.05 percent ceteth 20 and 3 percent glycerol oleate,
(h) 1 percent benzyl alcohol,
(i) water, and
(j) 10 percent cyclomethicone.

8. The composition of claim 4 comprising:
(a) 0.06 percent betamethasone dipropionate,
(b) 30 percent white petrolatum,
(c) 5 percent white wax,
(d) 10 percent solution of 70% sorbitol in water,
(e) 5 percent propylene glycol,
(f) 0.001 percent phosphoric acid and 0.3 percent monobasic sodium phosphate monohydrate,
(g) 1 percent polysorbate 60 and 4 percent sorbitan sesqui oleate,
(h) 0.1 percent 4-chloro-m-cresol,
(i) water, and
(j) 5 percent cyclomethicone.

* * * * *